US005538938A

United States Patent [19]
Duckworth

[11] Patent Number: 5,538,938
[45] Date of Patent: Jul. 23, 1996

[54] STABLE EMULSION FLOWABLE FORMULATION OF A 2-CHLOROACETAMIDE HERBICIDE AND AN IMIDAZOLINONE HERBICIDE

[75] Inventor: Charles A. Duckworth, Defiance, Mo.

[73] Assignee: Monsanto Company, St. Louis, Mo.

[21] Appl. No.: 323,310

[22] Filed: Oct. 14, 1994

[51] Int. Cl.$^6$ ..................................................... A01N 37/22
[52] U.S. Cl. ........................ 504/130; 504/139; 504/149; 71/DIG. 1
[58] Field of Search .................................. 504/139, 143, 504/130, 149; 71/DIG. 1

[56] References Cited

U.S. PATENT DOCUMENTS

| | | | |
|---|---|---|---|
| 4,731,109 | 3/1988 | Chupp | 71/118 |
| 4,755,218 | 7/1988 | Alt et al. | 71/94 |
| 5,268,352 | 12/1993 | Dexter | 504/206 |

OTHER PUBLICATIONS

The Agrochemicals Handbook, 3d Ed. "Imazaquin" The Royal Society of Chemistry, Pub., Aug.–1991.
Crop Protection Chemicals Reference 5th Ed (1989).

*Primary Examiner*—Brian M. Burn
*Attorney, Agent, or Firm*—Gordon Fred Sieckmann; Jon H. Beusen; Mark F. Wachter

[57] ABSTRACT

A composition and a method of preparing the same are provided wherein a 2-chloroacetamide herbicide is mixed with an imidazolinone herbicide to form a stable emulsion flowable formulation.

15 Claims, No Drawings

:5,538,938

STABLE EMULSION FLOWABLE FORMULATION OF A 2-CHLOROACETAMIDE HERBICIDE AND AN IMIDAZOLINONE HERBICIDE

BACKGROUND OF THE INVENTION

The present invention relates to a new and useful composition comprising a mixture of two or more herbicides and a method for preparing such a composition. More particularly, the present invention relates to a stable agriculturally acceptable herbicidal mixture of a 2-chloroacetamide herbicide dissolved in an organic solvent and an imidazolinone herbicide in acid form stably suspended as a separate phase in finely divided form and to a method for formulating such a mixture.

2-Chloroacetamide herbicides and especially 2-chloroacetanilide herbicides are known to be particularly useful when applied preemergent or early postemergent to control annual grasses and many broad-leaved weeds in a variety of crops, including cotton, corn, oilseed rape, peanuts, soybeans, sugarcane, etc.

Imidazolinone herbicides such as imazaquin are known to be especially effective when applied by means of preplant incorporation, preemergent and early postemergent techniques against broad-leaved and grass weeds and sedges to control weeds in soybeans, cowpeas, tobacco, etc. Unfortunately, formulated imazaquin loses an appreciable amount of its activity over passage of time. When 2-chloroacetamide herbicides and imidazolinone herbicides are used as mixtures, they complement each other's activity. Mixtures thereof provide desired control of a broader spectrum of weeds than that which can be controlled by the use of the 2-chloroacetamide herbicides alone or the imidazolinone herbicide alone. Unfortunately, formulations of the two herbicides prepared by conventional procedures are unstable, especially when the preferred acid form as distinguished from the water-soluble salt form of the imidazolinone herbicides is used. Difficulties in spraying such mixtures are commonly encountered. Heretofore, it has been found to be more convenient and effective to apply the two types of herbicides sequentially rather than to employ an unstable mixture of the two types of herbicides, even though spraying the two types of herbicides in a single application as a mixture affords obvious economic advantages over spraying the two types of herbicides as separate applications.

It is desirable, therefore, to prepare stable package mixes of a chloroacetamide herbicide and an imidazolinone herbicide which have extended shelf life and which can be conveniently sprayed on the plants to be controlled and wherein any reduction of activity due to chemical interaction between the two herbicides is substantially reduced.

Alachlor, which chemically is 2-chloro-2',6'-diethyl-N-methoxymethylacetanilide, and imazaquin, which chemically is (RS)-2-(4-isopropyl-4-methyl-5-oxo-2-imidazolin-2-yl) are two well-known herbicides used as preemergents which have individually enjoyed significant commercial success.

Alachlor technical is sold as Lasso® herbicide by Monsanto Company, St. Louis, Mo. and is used mainly as a pre-emergent herbicide.

Imazaquin is sold as Scepter® herbicide by American Cyanamid Co. (imazaquin-ammonium as 180 g/l acid equivalent).

While each of these herbicides has enjoyed commercial success individually, it is desired however to prepare a stable agriculturally acceptable concentrate composition comprising a herbicidally effective amount of each of alachlor and imazaquin which can be marketed as a concentrate and diluted with additional water and then applied in a single application to kill and control weeds or other vegetation in agriculture.

Package mixing of alachlor and imazaquin has not been successful heretofore because of the inherent instability of imazaquin in a neutralized salt form in the presence of alachlor, as well as because of the inability to stably suspend imazaquin in the acid form to provide a suitable emulsion. Forming mixtures of alachlor and imazaquin in which the imazaquin has been added as the ammonium salt may result in a composition, wherein the overall herbicidal activity of the two herbicides is substantially reduced. Attempts to develop mixtures of alachlor and imazaquin in which imazaquin was added as the solid acid form resulted in unacceptable formulations containing agglomerated imazaquin acid particles which during dilution with water, may result in clogging of sprayer nozzles and thus in reduction of effective weed control.

The process of this invention overcomes the above-discussed drawbacks of preparing a mixture of a 2-chloroacetamide herbicide and an imidazolinone herbicide by in-situ forming imazaquin acid particles during formulation of the mixture. The resulting imidazolinone acid particles are diminutive enough to remain stably suspended during storage of the mixture in concentrated form and later when used after dilution with water. These diminutive suspended particles do not clog sprayer nozzles; and the resulting spray provides herbicidal activity equivalent to sequential applications of a 2-chloroacetamide herbicide and an imidazolinone herbicide to weeds.

OBJECTS OF THE INVENTION

An objective of this invention is to prepare a stable emulsion flowable formulation of a 2-chloroacetamide herbicide and an imidazolinone herbicide.

Another object of the present invention is to provide a method of using a stable compatible mixture of at least one 2-chloroacetamide herbicide and at least one imidazolinone herbicide to control or kill weeds or other undesirable vegetation.

Another object of the present invention is to provide a process of forming a mixture of at least one 2-chloroacetamide herbicide and at least one imidazolinone herbicide.

These and other objectives of the invention are achieved in the process of this invention described more fully hereinafter.

BRIEF DESCRIPTION OF THE INVENTION

This invention comprises a process for preparing agriculturally acceptable stable emulsion flowable formulated concentrate or ready to use compositions containing an imidazolinone herbicide, for example, imazaquin and a 2-chloroacetamide herbicide, for example alachlor, compositions prepared by such process and a method of use for controlling undesirable annual and perennial plant species therewith using such compositions.

The composition of the present invention is a stable flowable herbicidally active formulation which comprises (1) about 30–40% by weight of a 2-chloroacetamide herbicide, preferably a 2-chloroacetanilide herbicide dissolved in an organic solvent; (2) about 1.5–3.0% by weight of an imidazolinone herbicide in acid form suspended as a finely divided solid in acid form; (3) about 20–35% water; (4) 20–35% of the inert solvent, and (5) the remainder being an acidic emulsifier, preferably a phosphated polyoxyalkylene alkyl phenol emulsifier containing up to 60 units of alkylene oxide, preferably about 4–30 ethylene oxide units. The alkylene oxide units may comprise ethylene oxide, propylene oxide, butylene oxide and combinations thereof. The pH of the composition is in the range of about 7.0–7.5 buffered preferably with monobasic potassium phosphate. The ratio of 2-chloroacetamide herbicide to organic solvent is in the range of from about 2:1 to about 1:1, and preferably from about 1.3:1 to about 1.2:1. The ratio of 2-chloroacetamide herbicide to emulsifier is in the range of from about 10:1 to about 5:1, preferably in the range from about 9:1 to about 8:1. The ratio of imidazolinone herbicide to buffer is in the range from about 20:1 to about 30:1, preferably in the range from about 23:1 to about 24:1.

In accordance with the process for preparing the composition of the present invention an agriculturally acceptable composition of a mixture of 2-chloroacetamide herbicide and an imidazolinone, an aqueous solution of a salt of an imidazolinone herbicide is provided and a solution of 2-chloroacetamide herbicide, inert organic solvent and an acidic emulsifier is provided. The two solutions are intimately mixed together to form a stable emulsion flowable herbicidal composition wherein the 2-chloroacetamide herbicide is dissolved in the organic phase and the imidazolinone herbicide is suspended in the water phase as a finely divided solid in acid form.

DETAILED DESCRIPTION OF THE INVENTION

A suitable 2-chloroacetamide herbicide is obtained from a source. The preferred 2-chloroacetamide herbicide is alachlor. Alachlor is heated to melt same and in a pre-mix tank is dissolved in a suitable inert organic solvent, such as Aromatic 200 obtainable from Exxon Chemical Company together with a suitable acidic emulsifier, such as a phosphated polyoxyalkylene alkyl phenol. Especially suitable is a phosphated nonylphenol having 6–12 units of ethylene oxide obtainable from Witco Corporation.

In a separate operation the selected imidazolinone herbicide is reacted in water in a mixing tank with a strong alkali, such as sodium or potassium hydroxide, to form an aqueous solution of the resulting salt of imidazolinone having a pH of above 7.5, for example 7.6–9.0. A solution of alachlor in an inert organic solvent is brought into intimate contact with the aqueous solution of the imidazolinone salt to form an emulsion flowable formulation which can be diluted with water and sprayed to the locus of the plants to be controlled. The addition of potassium phosphate monobasic acid may be used to buffer the composition to a pH of about 7.0 to about 7.5 with the result that the imidazolinone herbicide precipitates as the free acid in a finely dispersed stable form in the resulting liquid composition.

This invention is a multistep process which when carried out in accordance with this disclosure results in the preparation of a stable aqueous agriculturally acceptable emulsion flowable compositions comprising herbicidally effective amounts of each of alachlor or other suitable 2-chloroacetamide herbicide and imazaquin or other suitable imidazolinone herbicide.

In accordance with a specific embodiment of the present invention a stable emulsion flowable formation is provided by (a) preparing an imazaquin salt composition made by reacting imazaquin acid with a suitable base, such as NaOH in water, buffering this imazaquin salt to a pH in the range from about 7.0 to about 7.5 by addition of a buffer, such as potassium phosphate monobasic, (b) preparing an alachlor premix composition by admixing alachlor technical, a solvent and an acidic emulsifier, (c) admixing said imazaquin salt composition and alachlor premix composition in a vessel, such as a weigh tank to form a product composition while maintaining agitation and recirculation, (d) continuing agitation and recirculation of the product composition in the weigh tank, whereby formation and precipitation of imazaquin as the free acid is substantially complete; and then optionally (e) after sufficient recirculation and agitation, transferring the batch via a suitable disperser to a finished product vessel such as a tank, followed by optional filtration.

A herbicidally effective amount of both alachlor and imazaquin is present in a composition prepared by the process of this invention.

Typically the concentration of alachlor in a composition prepared by the process of this invention is in the range from about 100 to about 400 grams per liter and more preferably in the range from about 320 to about 380 grams per liter of composition by weight.

A herbicidally effective application rate of alachlor is in the range from about 2.2 to about 4.5 kilograms per hectare and more preferably in the range from about 2.6 to about 3.9 kilograms per hectare. Those of skill in the art will recognize that the application and use rates provided by the label for Lasso® herbicide will be useful in determining the application rates for a composition prepared by the process of this invention.

Alachlor technical is available from Monsanto as Lasso® herbicide or may be prepared by the process disclosed in U.S. Pat. Nos. 3,442,945 and 3,547,620.

Typically, the concentration of imazaquin in a composition prepared by the process of this invention is in the range from about 20 to about 30 grams (acid equivalent) per liter and more preferably in the range from about 22 to about 24 grams (acid equivalent) per liter of composition by weight.

A herbicidally effective application rate of imazaquin is in the range from about 20 to about 500 grams per hectare (acid equivalent) and more preferably in the range from about 60 to about 400 grams per hectare (acid equivalent). Those of skill in the art will recognize that the applications given on the label for Scepter® herbicide is useful for applying a composition prepared by the process of this invention.

Solvents which may be used in the process of this invention include: chlorinated or non-chlorinated petroleum hydrocarbons, although non-chlorinated aromatic petroleum hydrocarbons are preferred.

Most preferred solvents include Aromatic 100, Aromatic 150 and Aromatic 200 solvents.

The weight ratio of alachlor technical to solvent is in the range from about 2:1 to about 1:1 and preferably from about 1.3:1 to about 1.2:1.

The weight ratio of alachlor technical to emulsifier is in the range from about 10:1 to about 5:1 and preferably in the range from about 9:1 to about 8:1.

Illustrative preferred acidic emulsifiers which may be employed in the process of this invention include phosphate ester type with 4–30 moles ethylene oxide although phosphate ester type with 5–6 moles ethylene oxide are more preferred and FloMo 6 moles ethylene oxide 6NP is most preferred.

Salts of imazaquin which may be employed include potassium, ammonium and sodium. Preferred salts include potassium and sodium, while sodium salts are the most preferred as a starting material.

These salts may be prepared by first reacting the imazaquin in acid form with a suitable base.

Illustrative buffers which can be employed include effective phosphate or benzoate compounds, although potassium phosphate monobasic is most preferred.

Phosphate buffers are available from Ashland Chemical.

The ratio of imazaquin to water is in the range from about 1:5 to about 1:20 and preferably in the range from about 1:10 to about 1:12 by weight.

The ratio of imazaquin to base is in the range from about 2:1 to about 5:1 and preferably from about 3:1 to about 4:1.

The ratio of imazaquin to buffer is in the range from about 20:1 to about 30:1 and preferably in the range from about 23:1 to about 24:1.

In another step subsequent to the above steps, it is preferred to first charge a suitable formulation vessel with process water.

Typically, the buffered sodium imazaquin solution next is added to a formulation vessel.

The formulation vessel can be any suitable vessel including but not limited to stainless steel tanks. The preferred formulation vessel is a stainless steel closed top tanks and stainless steel closed top tanks fitted with weight sensors and means for agitation is most preferred as a formulation vessel.

The alachlor premix prepared as described above is then added to the formulation vessel.

The resulting composition in the formulation vessel is agitated and recirculated for about 20 minutes, during which time emulsion formation and recrystallization of imazaquin (as acid) in finely divided form take place.

Any convenient method of agitation may be employed to achieve emulsion formation and precipitation of imazaquin acid particles in finely divided form.

The term "recirculation" as employed herein includes any process which in an equivalent fashion results in thorough mixing of the contents of the formulation vessel. Typically, preferable recirculation processes include mixing from the bottom of tank out and recycling from the top of the tank back to the bottom of the tank.

One of skill in the art will understand when emulsion formation occurs as the composition of oil phase (alachlor premix) including appropriate surfactants are mixed with the water (imazaquin) phase.

The composition is then preferably transferred via a disperser, such as a one-stage Tekmar disperser, to a product release vessel, followed by filtering, preferably through 100-mesh, high-speed vibrating screens to efficiently remove large particles and any solid foreign material.

Typical means of filtering include filter screens (Sweco) or filter socks fitted into piping although alternative techniques such as basket strainers may be suitably employed.

The process of this invention is normally carried out at room temperature and atmospheric pressure, although greater or lesser temperatures and pressures may be employed.

The composition of the invention is applied to the vegetation to be controlled in a herbicidally effective amount, such as by spraying in a conventional manner. A broad spectrum of grasses, broadleaf weeds and sedges can be controlled in a variety of crops.

As an example for practicing the process of this invention, the amounts of ingredients for making a large quantity of an alachlor/imazaquin composition by this invention are given as follows. It is to be understood that the working examples given herein for the practice of the invention are merely illustrative and the invention is not limited thereto. Unless otherwise indicated all percentages are given on a weight basis.

The following materials were used to formulate 7.56 cubic meters of a composition of this invention.

| Ingredients | Weight Percent | Weight Kilograms |
|---|---|---|
| Alachlor* (94.5%) | 36.3 | 288.9 |
| Imazaquin* (97.7%) | 2.2 | 176.4 |
| Aromatic 200 | 30.0 | 139.0 |
| FloMo 6NP | 4.5 | 358.5 |
| T-H Antifoam 30 IND | 0.03 | 2.0 |
| NaOH (50% w/w) | 0.60 | 48.1 |
| Potassium phosphate monobasic | 0.09 | 7.3 |
| Water | 26.3 | 209.6 |

*Technical grade of active ingredients.

RAW MATERIALS

The raw materials used in the above formulation process and the suppliers thereof are as listed below.

A. 2-Chloro-2',6'-diethyl-N-(methoxymethyl)-acetanilide: Alachlor, available from Monsanto Company, Muscatine, Iowa.

B. (RS)-2-(4-'isopropyl-4-methyl-5-oxy-2-imidazolin-2-yl) quinoline-3-carboxylic acid: Imazaquin available from American Cyanamid Co.

C. Aromatic 200 solvent is available form Exxon Co. USA.

D. Flomo 6NP emulsifier is available from Witco Corporation and is a phosphated nonylphenol containing an average of 6 ethylene oxide units and having an acid pH.

E. T-H Silicone Antifoam 30 IND is available from Thompson-Hayward Chemical Co.

F. NaOH 50% (w/w) is available from Vulcan, Hooker Chemical or BASF.

G. Monobasic Potassium Phosphate is available from Ashland Chemical Co.

PROCESS DETAILS

A 12% (acid equivalent) sodium imazaquin solution is prepared by reaction of imazaquin acid with sodium hydroxide in water, followed by buffering to a pH of about 7.0–7.5 with monobasic potassium phosphate. The ingredients used to prepare this solution are as follows:

| SODIUM IMAZAQUIN SOLUTION | |
|---|---|
| | Weight % |
| Imazaquin (97.7%) | 12.29 (12.00) |
| NaOH 50% w/w | 3.35 |

| SODIUM IMAZAQUIN SOLUTION | |
|---|---|
| | Weight % |
| Potassium phosphate | 0.52 |
| Antifoam 30 IND | 0.14 |
| Water | 83.70 |

Based on the amount of solution to be prepared (907 kg required per batch), the tank is charged with the appropriate amount of process water. Sodium hydroxide solution and antifoam are added and agitation is begun. Slowly imazaquin tech is added to the tank under agitation. During this step, a 5°–10° C. or so temperature increase occurs due to reaction of imazaquin acid with NaOH. Agitation of the vessel is continued until no solid imazaquin is present and pH measurements indicate that the pH had stabilized at about 9–9.5. Following complete reaction of the imazaquin acid to the sodium salt, the solution pH is buffered to about 7.0–7.5 by addition of potassium phosphate monobasic to the vessel based on the weight percentage above. The sodium imazaquin solution is ready for use in preparing the formulation.

Adjustments in the amount of imazaquin acid and NaOH used to prepare the salt solution will vary depending on the assay of the imazaquin technical. Addition of small amounts of sodium hydroxide or potassium phosphate may be required if the pH of the solution is not in the 7.0–7.5 range.

B. Organic Premix Preparation

Alachlor technical, Aromatic 200 solvent and FloMo 6NP emulsifier are intimately mixed to prepare an organic premix composition containing 51.5% alachlor technical, 42.2% solvent and emulsifier.

The following sequence of additional processing steps can be used to prepare the compositions of the present invention.

1. A check is made to determine that the alachlor premix temperature is below about 35° C. to prevent invert emulsion formation during preparation and above about 10° C. to prevent alachlor crystallization.

2. Add process water to the weigh tank

3. Add sodium imazaquin solution to the weigh tank and then begin agitation and recirculation in the tank.

4. Add alachlor premix to the weigh tank while maintaining agitation and recirculation.

5. After all of the alachlor premix is added to the weigh tank, continue agitation and recirculation for about an additional 20 minutes to allow for complete emulsion formation and precipitation of imazaquin as the free acid in the form of suspended finely divided solid particles.

6. Addition of small amounts of potassium phosphate to finished batches may be necessary if product pH is above about 6.5.

Precipitation of imazaquin as the free acid during the emulsion formation phase of the process is achieved.

By adjusting the final pH of the formulation prepared in accordance with the process of this invention is to be in the range from about 5.5 to about 6.5 and preferably from about 6.0 to about 6.2.

Although FloMo 6Np surfactant is preferred to form the emulsion flowable formulation of the present invention and to provide the pH adjustment for the in situ reformation of the imidazolinone herbicide from the water soluble form to a suspended finely-divided solid acid form, any suitable emulsifier having a suitable low pH can be used. Examples of useful surfactants for these purposes include, for example sulfated polyoxyalkylene alkylphenol; alcohol sulfates and polyoxyalkylene alcohol sulfates; mono- and di- alcohol sulfates; mono- and di-(polyoxyalkylene alcohol) phosphates; mono- and di-(polyoxyalkylene alkylphenol) phosphates; polyoxyalkylene alkylphenol carboxylates and polyoxyalkylene alcohol carboxylates, said compounds each containing up to about 60 moles of an alkylene oxide group and alkyl and alcohol groups having from about 8 to about 20 carbon atoms. The preferred alkylene oxide group is ethylene oxide. The number of ethylene oxide units is preferably from about 8 to about 20 per molecule.

A herbicide composition prepared in accordance with the process of the present invention is capable of controlling various weeds in an agricultural field such as a field designated for growing soybeans or imazaquin resistant corn by soil treatment before the emergence of weeds.

If desired, the composition of the present invention may be used in combination with insecticides, fungicides, other herbicides, plant growth controlling agents, fertilizers or like agrochemicals.

Fertilizers useful in combination with the active ingredients include, for example ammonium nitrate, urea, potash and superphosphate. Other useful additaments include materials in which plant organisms take root and grow such as compost, manure, humus, sand and the like.

The amount of a composition prepared in accordance with the present invention to be applied may vary depending on the types of crops and weeds to be treated, the weather conditions, the type of formulations, the mixing ratio of the active ingredients, the application method, the application site, timing, etc.; but it is applied generally in a dose of from 25 to 500 g, preferably from 50 to 300 g of the total active ingredients per hectare.

The invention in the working example above has been illustrated using the herbicidal mixture of alachlor as a suitable 2-chloroacetamide herbicide and imazaquin as a suitable imidazolinone herbicide. However, among other suitable herbicidally active 2-chloroacetamides are acetochlor, butachlor, butenchlor, dimethachlor, metazachlor, metolachlor, and propochlor.

Among other suitable herbicidally active imidazolinone herbicides are imazamethabenz-methyl, imazapyr, and imazethapyr.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A stable emulsion flowable herbicidal formulation concentrate comprising:

a) about 30–40% by weight of a 2-chloroacetamide herbicide, b) about 1.5–3.0% by weight of an imidazolinone herbicide, c) about 20–35% by weight water, d) about 20–35% inert organic solvent, and e) an acidic emulsifier, said 2-chloroacetamide herbicide being dissolved in the organic phase and said imidazolinone herbicide in acid form being suspended as a finely divided solid in the composition.

2. The formulation of claim 1 wherein the 2-chloroacetamide herbicide is a 2-chloroacetanilide herbicide.

3. The formulation of claim 2 wherein the 2-chloroacetanilide is alachlor, acetochlor or metolachlor.

4. The formulation of claim 1 wherein the imidazolinone herbicide is imazaquin, imazapyr or imazethapyr.

5. The formulation of claim 1 wherein the acidic emulsifier is sulfated polyoxyalkylene alkylphenol, alcohol sulfate, polyoxyalkylene alcohol sulfate, mono- or di- alcohol phosphate, mono- or di-(polyoxyalkylene alcohol) phosphate, mono- or di-(polyoxyalkylene alkylphenol) phosphate, polyoxyalkylene alkylphenol carboxylate, or polyoxyalkylene alcohol carboxylate, each emulsifier containing up to about 60 moles of an alkylene oxide group and alkyl and alcohol groups having from about 4 to about 30 carbon atoms.

6. The formulation of claim 5 wherein the emulsifier is a phosphated nonylphenol ethoxylate.

7. The formulation of claim 1 additionally containing a pH buffer.

8. The formulation of claim 7 wherein the buffer is monobasic potassium phosphate.

9. The composition of claim 1 wherein the ratio of 2-chloroacetamide herbicide to organic solvent is in the range of from about 2:1 to about 1:1.

10. The composition of claim 1 wherein the ratio of 2-chloroacetamide herbicide to emulsifier is in the range of from about 10:1 to about 5:1.

11. The composition of claim 7 wherein the ratio of the imidazolinone herbicide to buffer is in the range from about 20:1 to about 30:1.

12. A stable emulsion flowable herbicidal formulation comprising:

a) about 30–40% by weight of alachlor, b) about 1.5–3.0% by weight of imazaquin, c) about 20–35% by weight water, d) about 20–35% by weight aromatic petroleum hydrocarbon solvent, e) a phosphated nonylphenol having about 4–30 ethylene oxide units, wherein the alachlor is dissolved in the solvent and the imazaquin is suspended as a finely divided solid.

13. The formulation of claim 12 wherein monobasic potassium phosphate is present as a buffering agent.

14. A method of controlling or killing weeds which comprises applying a herbicidally effective amount of the herbicidal composition of claim 1.

15. A process of preparing an agriculturally acceptable composition of a mixture of a 2-chloroacetamide herbicide and an imidazolinone herbicide comprising the steps of:

a) providing an aqueous solution of a salt of an imidazolinone herbicide;

b) providing a solution of a 2-chloroacetamide herbicide, inert organic solvent and, c) intimately mixing the above solutions with an acidic emulsifier to form a stable emulsion flowable herbicidal composition wherein the 2-chloroacetamide herbicide is dissolved in the organic phase and the imidazolinone herbicide is suspended in the composition as a finely divided solid and is converted to the acid form.

* * * * *